United States Patent
Kim

(10) Patent No.: US 8,518,233 B2
(45) Date of Patent: Aug. 27, 2013

(54) MANUFACTURING METHOD OF MEDICAL STERILIZED ISOTONIC SOLUTION HAVING LOW-CONCENTRATEDLY CONTROLLED FREE CHLORINE INCLUDING HYPOCHLOROUS ACID THEREIN

(76) Inventor: Chil-Young Kim, Gyeonggi-do (KR)

(*) Notice: Subject to any disclaimer, the term of this patent is extended or adjusted under 35 U.S.C. 154(b) by 899 days.

(21) Appl. No.: 12/449,596

(22) PCT Filed: Feb. 26, 2008

(86) PCT No.: PCT/KR2008/001096
§ 371 (c)(1),
(2), (4) Date: Aug. 14, 2009

(87) PCT Pub. No.: WO2008/105613
PCT Pub. Date: Sep. 4, 2008

(65) Prior Publication Data
US 2009/0317491 A1    Dec. 24, 2009

(51) Int. Cl.
*C02F 1/467* (2006.01)
(52) U.S. Cl.
USPC ............ 205/556; 205/701; 205/742; 205/744
(58) Field of Classification Search
USPC .................................. 205/556, 701, 742, 744
See application file for complete search history.

(56) References Cited

U.S. PATENT DOCUMENTS

| 4,710,233 A | * | 12/1987 | Hohmann et al. | ............ 205/701 |
| 6,117,285 A | * | 9/2000 | Welch et al. | .................. 204/237 |

FOREIGN PATENT DOCUMENTS

| JP | 06-237747 | 8/1994 |
| JP | 2004-148108 | 5/2004 |
| KR | 10-325677 | 2/2002 |
| KR | 10-2007-118402 | 12/2007 |
| WO | WO2006/115370 | 11/2006 |

OTHER PUBLICATIONS

Nakajima et al., Evaluation of disinfective potential of reactivated free chlorine in pooled tap water by electrolysis, (2004)Journal of Microbiological Methods 57 pp. 163-173.*

* cited by examiner

*Primary Examiner* — Arun S Phasge
(74) *Attorney, Agent, or Firm* — Kusner & Jaffe

(57) ABSTRACT

The present invention relates to a manufacturing method of medical sterilized normal saline, more specifically, to such a method for manufacturing sterilized normal saline for medical purpose with effective sterilizing efficacy comprising: a step of disposing at least one electrode set immersed in saline solution of pH 4.0 to pH 7.5 including a pair of electrodes with flat surface separated from each other by an interval between 1 mm and 3 mm, the flat surfaces of the electrodes facing each other; and a step of supplying 30 mA to 200 mA direct current to the electrodes by applying 2.4V to 3.3V DC power to the electrodes; wherein free chlorine is reliably and stably generated as having concentration range between 0.17 ppm and 6 ppm from electrolysis between electrodes.

12 Claims, 10 Drawing Sheets

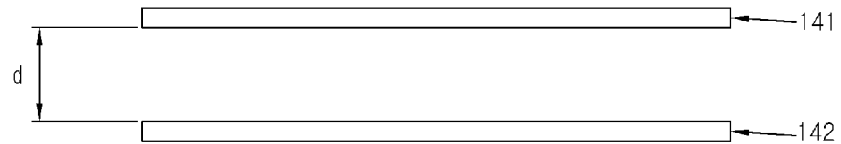
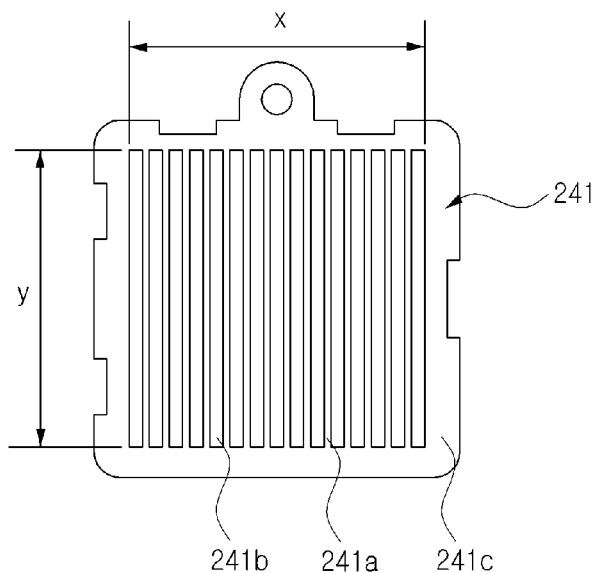
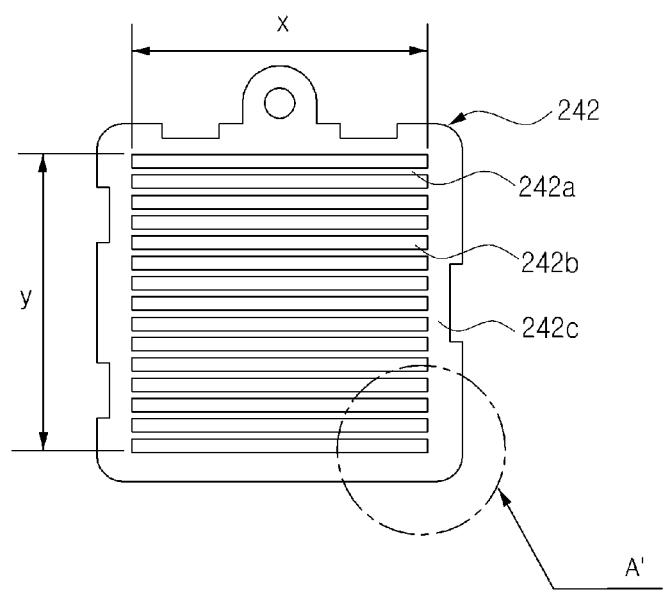

MANUFACTURING METHOD OF MEDICAL STERILIZED ISOTONIC SOLUTION HAVING LOW-CONCENTRATEDLY CONTROLLED FREE CHLORINE INCLUDING HYPOCHLOROUS ACID THEREIN

TECHNICAL FIELD

The present invention relates to a manufacturing method, more particularly, to such a method reliably manufacturing low-concentratedly controlled free chlorine including hypochlorous acid (HOCl) therein using electrolysis in order to disinfect various germs causing diseases.

BACKGROUND ART

As is well known, environmental diseases have been increased as air and soil has been polluted, and the concern for a well-being and health has been increased. Accordingly, rhinitis' patients washing their noses with normal saline in the market have been increased.

Hypochlorous acid (HOCl) is well known as effective and harmless chemicals to people as well as chemicals for disinfecting various viruses. However, Journal of Burns and Wounds, a medical journal published on Apr. 11, 2007, showed in its article titled "Hypochlorous Acid as a Potential Wound Care Agent" that HOCl has never been used as medical supplies for curing viral infection.

On the other hand, normal saline is achieved by four chemical mechanisms as follows.

$$Cl_2 + H_2O \longleftrightarrow HOCl + H^+ + Cl^-$$ Chemical equation 1

$$Cl_2 + H_2O \longleftrightarrow HOCl + H^+ + Cl^-$$ Chemical equation 2a

$$Cl_2 + H_2O \longleftrightarrow HOCl + H^+ + Cl^-$$ Chemical equation 2b

$$OCl^- + H^+ \longleftrightarrow HOCl$$ Chemical equation 3

That is, HOCl can be generated by hydrolyzing chlorine gas in accordance with the chemical equation 1, or by electrolyzing saline solution in accordance with the chemical equation 2a and 2b, or by oxidizing hypo-chlorite in accordance with the chemical equation 3. In the case of chemical equation 1, however, it is troublesome and risky to handle chlorine gas which is sometimes in the form of poisonous gas. Also, with regard to the chemical equations 2a and 2b, it is written in the above article that it is very difficult to realize the targeted concentration of HOCl by electrolysis. Therefore, the above journal shows that it is most desirable to generate HOCl for medical uses through using commercially available hypo-chlorite in accordance with the chemical equation 3.

On the other hand, it is written at 71 page of the above journal that the minimum bactericidal concentrations (MBC) of HOCl enough to disinfect viruses at normal temperature are shown as follows.

TABLE 1

| Germs | MBC (ppm) |
| --- | --- |
| Escherichia coli | 0.7 |
| Pseudomonas aeruginosa | 0.35 |
| Staphylococcus aureus | 0.173 |
| Staphylococcus epidermidis | 0.338 |
| Micrococcus luteus | 2.77 |
| Corynebacterium amycolatum | 0.169 |
| Haemophilus influenzae | 0.338 |
| Proteus mirabilis | 0.340 |
| Staphylococcus hominis | 1.4 |

TABLE 1-continued

| Germs | MBC (ppm) |
| --- | --- |
| Staphylococcus haemolyticus | 0.338 |
| Staphylococcus saprophyticus | 0.35 |
| Candida albicans | 2.7 |
| Klebsiella pneumoniae | 1.7 |
| Serratia marcescens | 0.169 |
| Sterptococcus pyogenes | 0.169 |
| Enterobacter aerogenes | 0.676 |
| Candida albicans | 0.17 |
| Methicillin-resistent Staphylococcus aureus | 0.682 |
| Vancomycin-resistent Enterococcus faecium | 2.73 |

From the above table 1, even very low concentration of HOCl can sterilize most of germs effectively. However, a solution with unlimitedly higher concentration of HOCl would not be used for medical uses. Therefore, the above journal describes that the unreliable amount of HOCl generated by an electrolysis cannot be used for medically curing any infection such as by directly injecting or spraying it into a human body. Specifically, when the concentration of HOCl exceeds over 6 ppm, it causes trouble on sensitive parts of human body such as a mucosa of a nose and eyes, further it causes the stench of the solution, and thus, a solution with over 6 ppm concentration of HOCl has been regarded as not being used for medical treatment. In this regard, the document published on January in 1994 by the U.S. Environmental Protection Agency has also announced that a desirable concentration of the free chlorine (in other words, it is referred as 'residual chlorine') for an adult with weight of 70 Kgf is recommended as less than 6 ppm.

Therefore, it is most important to manufacture sterilized normal saline with maintaining the precise low concentration of free chlorine including HOCl in order for applying HOCl to a medical treatment. Also, maximizing the ratio of HOCl in the free chlorine is needed for better sterilizing effect.

On the other hand, HOCl has a relatively long half-life time of 44 hour in the inside of a human body. However, in the water, as shown in FIG. 16, the half-life time of HOCl falls to 3 minutes, and thus, the effective sterilizing efficacy of HOCl cannot be expected after the half-life time is passed.

Considering above, HOCl has been widely admitted for its possible use for medical treatments because HOCl has a sterilizing efficacy against diverse germs. However, as HOCl has very short half-life time outside of human body, and as HOCl has not been realistically manufactured with being controlled within the predetermined lower range of concentration, it has been regarded as impossible to apply HOCl to patients for medical purpose such as treating diseases infected by diverse germs.

Accordingly, there has been great need for method of manufacturing HOCl with the predetermined constant lower range of concentration enough to terminate germs as well as not to cause the disgusted feeling to patents so that the free chlorine especially including HOCl can be realistically applied to patents for medical purpose.

DISCLOSURE OF INVENTION

Technical Problem

These disadvantages of the prior art are overcome by the present invention. It is an object of the present invention to provide a method for sterilized normal saline for medical purpose with the constantly and reliably controlled as low concentration between 0.17 ppm and 6 ppm so that the sterilized normal saline has effective sterilizing efficacy without causing patients to feel disgusted.

Another object of the present invention is to provide a method for sterilized normal saline for medical purpose with the regularly controlled concentration of free chlorine which is inodorous so that it does not make trouble on diseases such as a mucosa of a lung, eyes, a nose or a skin and therefore can be comfortably used for sensitive patients.

Still another object of the present invention is to provide a portable apparatus for manufacturing sterilized normal saline for medical purpose so that patients can use the sterilized normal saline for their treatment immediately after manufacturing, which includes HOCl having a short half-life time outside of human body.

Therefore, users can manufacture the sterilized normal saline with lowly controlled concentration of HOCl everywhere they want so that the manufactured normal saline can be applied to various parts such as an inflammation, an athlete's foot, atopic dermatitis, etc.

Yet another object of the present invention is to provide a portable apparatus for manufacturing normal saline having controlled lowly concentrated HOCl generated from the electrolysis by applying low electric current and low voltage so that the life time of batteries can be prolonged.

Still, another object of the present invention is to provide a method for manufacturing sterilized normal saline by electrolysis with using subacid or neutral water of pH 4.0 to pH 7.5 in order to raise the ratio of HOCl with strong sterilizing efficacy.

Technical Solution

In order to attain the above mentioned object, the present invention provides a method for manufacturing sterilized normal saline for medical purpose with effective sterilizing efficacy comprising: a step of disposing at least one electrode set immersed in saline solution of pH 4.0 to pH 7.5 including a pair of positive electrode and negative electrode with flat surface separated from each other by an interval between 1 mm and 3 mm, the flat surfaces of the electrodes facing each other; a step of supplying 30 mA to 200 mA direct current to the electrodes by applying 2.4V to 3.3V DC power to the electrodes; wherein free chlorine is generated as having concentration range between 0.17 ppm and 6 ppm from electrolysis between electrodes.

As the medical normal saline of the present invention is manufactured by use of subacid or neutral normal saline of pH 4.0 to pH 7.5, as shown in FIG. 13, the ratio of HOCl in the solution having experienced the electrolysis can be maximized at least 50% or up to 100% thereof, thereby achieving high treatment efficacy even with the small amount of the free chlorine and also preventing the acid degree of the solution from causing patients to feel troublesome at their mucosa of nose or eyes. Further, the medical normal saline of the present invention can be manufactured by mixing salt and tap water or underground water of subacid or neutral pH which can be easily obtained.

Herein, the solution can have its up to 3% high salt concentration different from the normal saline so that the solution of high concentration may be supplied to insensitive organs of human body which are not sensitive.

When the gap of the pair of the electrodes is less than 1 mm, the current between the electrodes is excessively raised, and gases generated during the electrolysis cannot get out of the inner space between the electrodes, and thus, the free chlorine is sometimes generated too much or is sometimes generated too little. That is, the amount of the free chlorine generated thereduring is not consistent when the gap of the electrodes is less than 1 mm. When the gap of the pair of the electrodes is over 3 mm, high electric current is required to flow between the pair of electrodes. However, when the high electric current is supplied to the pair of the electrodes, the current becomes excessively increased as shown in FIG. 14 and thus it becomes impossible to make low current flow between the electrodes so that the controlled small amount of the free chlorine cannot be generated, and also, the consumption of the electric power becomes too much so that it cannot be applied to a portable device. That is, in order that the controlled low concentrated free chlorine can be reliably generated by the electrolysis, it is required to constantly maintain the current and the amount of electric charges moving across the electrodes to be very low.

With maintaining the gap between the electrodes, when the DC voltage between 2.4V and 3.3V is applied thereto, DC current between 30 mA and 200 mA flows therebetween. When the DC current continues to flow between the electrodes, solution with the controlled low concentration between 0.17 ppm and 6.0 ppm of free chlorine is obtained. Herein, when DC voltage less than 2.4V is applied to the electrodes, as the voltage difference cannot overcome the resistance of the normal saline and thus the electric current cannot flow between the electrodes. When DC voltage more than 3.3V is applied to the electrode, it becomes very difficult to maintain the DC current within the constant range because the current between the electrodes increases very sharply, and thus, the concentration of the free chlorine also increases sharply, and accordingly, it becomes very difficult to generate the controlled low concentrated free chlorine.

In this regards, the net current to an external circuit via one electrode is determined by the difference between the oxidation current and the deoxidation current. Specifically, as shown in FIG. 14, according to Butler-Volmer equation, the net current increases proportionally when the overvoltage is small while the net current exponentially increases when the overvoltage is larger than a predetermined value. That is, the current flowing between the electrodes immersed in the saline solution having concentration of 0.3% to 3% depends on the voltage applied thereto and the resistance between the electrodes. Therefore, as saline solution between the electrodes having the simple flat surface respectively plays a role in an electric resistance, electric current will not flow when small voltage less than DC 2.4V is applied to the electrodes. On the other hand, when large voltage more than DC 3.3V is applied thereto, excessive large electric current will flow therebetween and excessive amount of the free chlorine is generated within very short time and thus it becomes very difficult to control the concentration of the free chlorine to be lower range.

The normal saline having lowly controlled concentration of the residual chlorine can be reliably and stably manufactured by applying DC low current and low DC voltage. The normal saline manufactured by the above method is not irritative and does not have sickening smell and thus can be used in the wide range of usage for medical purpose such as lung, eyes, nose and skins without causing patients to feel disgusted.

Herein, as normal saline manufactured by the present invention is neutral or subacid, the most part of the free chlorine generated during the electrolysis becomes HOCl having strong sterilizing efficacy. It is desirable to preset the concentration of the free chlorine between 3 ppm and 4 ppm thereby minimizing the possibility that the concentration of the free chlorine exceeds 6 ppm.

The mechanism of manufacturing the medical normal saline with oxidants such as ozone ($O_3$), hydrogen peroxide ($H_2O_2$), OH-radicals, HOCl, $OCl^-$ of the present invention is realized by the following (1) to (5) procedures.

(1) The process of ozone creation starts from electrolysis of $H_2O$ and finished with a combination of O and $O_2$.

$$*H_2O \rightarrow H^+ + (OH)_{ads} + e^-$$

$$(OH)_{ads} \rightarrow (O)_{ads} + H^+ + e^-$$

$$2(OH)_{ads} \rightarrow O_2 + 2H^+ + 2e^-$$

$$2(O)_{ads} \rightarrow O_2$$

$$(O)_{ads} + O_2 \rightarrow O_3$$

(2) $H_2O_2$ is made by a direct process of electrolysis of $O_2$ and indirect process of a combination of OH radicals, a medium generated by $O_3$. That is, direct course, $$O_2 + e^- \rightarrow O_2^-$$

$$O_2 + 2H^+ + 2e^- \rightarrow H_2O_2$$

Indirect course, $$OH\cdot + OH\cdot \rightarrow H_2O_2$$

(3) HOCl is formed by chemical reaction with H2O after combining with $Cl^-$ existing in water with $Cl_2$.

$$2Cl^- \rightarrow Cl_2 + 2e^-$$

$$2H_2O + 2e^- \rightarrow H_2 + 2OH^-$$

$$*Cl_2 + H_2O \rightarrow HOCl + H^+ Cl^-$$

(4) OH radicals are created and vanished too soon to measure it directly, but in the case of ozone existing in water, OH radicals are finally created forming radical chain cycle with reacting with $HO_2^-$, conjugate base of $H_2O_2$, or $OH^-$.

$$O_3 + OH^- \rightarrow \text{Radical Chain Reaction} \rightarrow OH\cdot$$

$$O_3 + HO^{2-}(\text{conjugate base of } H_2O_2) \rightarrow \text{Radical Chain Reaction} \rightarrow OH\cdot$$

(5) Microorganisms existing in water get removed or inactivated by the oxidants, the following microorganism is removed by electroadsorption and the following microorganics gets removed by direct electrolysis reacting with $e^-$.

That is, regarding the microorganism, $$M(\text{Microorganism}) \rightarrow \text{Electrosorption} \rightarrow \text{Inactivation}$$

Also, $$M(\text{Microorganism}) + O_3 \rightarrow \text{Inactivation}$$

$$M + OH\cdot \rightarrow \text{Inactivation}$$

$$M + HOCl \rightarrow \text{Inactivation}.$$

And, regarding microorganics, $$M(\text{Microorganics}) + e^- \rightarrow M-$$

Also, $$M(\text{Microorganics}) + O \rightarrow \text{Product}$$

$$M + OH\cdot \rightarrow \text{Product}$$

$$M + HOCl \rightarrow \text{Product}$$

That is, during electrolysis, oxidation or sterilization is actively performed by the various oxidants including the free chlorine such as HOCl, $OCl^-$ formed in the (1) to (5) procedures. During and after the electrolysis, germs are killed by the sterilizing efficacy of HOCl contained in the medical normal saline as the majority of the free chlorine is generated during the electrolysis.

Here, $H_2O_2$ generated in the procedure of electrolysis can make free radicals, $HO\cdot + O\cdot$ and these free radicals decompose proteins into peptide and amino acid with low molecular weight so that protein turns into water-soluble substance and converges on a double-bonded area, and epoxide is formed. (For instance, C=C—R become C—C—R) More specifically, free radicals formed in $H_2O_2$ have high reactivity and attacks other organic molecules like protein for stability of itself hereby oxidization of $H_2O_2$ decomposes protein into amino acid, water-soluble substance and remove protein, one of causes for allergies.

That is, the oxidants including the free chlorine generated during the electrolysis of the present invention has a strong efficacy of killing germs, fungi, bacteria and viruses as well as an efficacy of decomposing the double-bonded area between carbon molecules and nitrogen molecules thereby removing proteins to cause allergy and atopy dermatitis. Therefore, the medial normal saline of the present invention can be applied to treatment of allergy or atopy dermatitis. Further, the medical normal saline of the present invention can be used for curing rhinitis and atopy by transforming the protein to provoke an allergy. Also, the free chlorines such as HOCl are effective at curing HPV (human papillomavirus) to provoke uterine cancer, and thus can be supplied into the womb.

On the other hand, the inventor of the present invention newly found that the concentration of the free chlorine can be precisely controlled by converting the direction of the electric current between the electrodes during the electrolysis. Specifically, in case that the electric current is supplied to the electrodes without converting the direction thereof during the electrolysis, the experiment shows that the free chlorine is generated more rapidly and suddenly, and that the concentration of the free chlorine becomes different with one another as having larger variations in accordance with each experiments compared with the cases with converting the direction of the electric current. In order to increase the effect of converting the DC current, the period of converting DC current is desired to be set 1 second to 20 seconds. In case that the period is set over 20 seconds, the effect thereof becomes insignificant. Also, considering that the procedure of manufacturing the small amount less than 100 ml of sterilized medical normal saline with the free chlorines by supplying DC current to electrodes is realized for 20 seconds to 60 seconds, it is effective that the period is not over 20 seconds.

The method of the medical normal saline of the present invention can be realized just with a container for accommodating normal saline, electrodes in the container and a power supply to supply DC current to the electrodes. Thus, the method of the present invention can be achieved by a light apparatus having only a few requisite components. Therefore, the method of the present invention can be realized as a portable apparatus to be used not only by professional medical institutions but also by an individual patient, i.e., customer level.

Especially, HOCl generated in the medical sterilized normal saline is very unstable in neutral or subacid area, and thus is tend to be reduced to a half only for 3 minutes. Therefore, the free chlorines should be supplied to patients within 3 minutes from manufacturing the medical normal saline. From this point of view, by realizing the method of the present invention by a portable apparatus, many patients or customers can use the medical normal saline to to-be-cured region such as inside of nose, eyes, skins of allergy, teeth, teethridge, lung, throat, bronchi, womb, etc., until the free chlorines do not lose the most of sterilizing efficacy, i.e., right after manufacturing the medical normal saline for themselves. Once HOCl is supplied to the inside of mammal bodies, the half-life time of HOCl increases to 44 hours. Therefore, prompt supply into the body right after manufacturing the medical normal saline can obtain enough time to sterilize or kill germs, fungi, bacteria, the causes of diseases.

On the other hand, the present invention provides a method for manufacturing sterilized normal saline for medical purpose with sterilizing efficacy comprising: a step of disposing at least one electrode set immersed in saline solution of pH 4.0 to pH 7.5 including a pair of electrodes, each of which has a plurality of domains separated from one another on the facing surface of the each electrode, the plurality of domains on the facing surface of the one electrode being faced to the plurality of domains respectively on the facing surface of the other electrode with an interval between 1 mm and 3 mm; a step of supplying 30 mA to 180 mA of DC current to the electrodes by applying 2.2V to 3.2V DC voltage to the electrodes; and a step of converting the direction of DC current between the electrodes at least one time, wherein the total area of the plural domains of each of the electrodes covers 4% to 25% of the total area of the facing surface of each electrode and the free chlorine is generated as having concentration range between 0.17 ppm to 6 ppm during the electrolysis.

That is, a plurality of domains are formed on the surface of the electrodes which faces each other, and a plurality of current paths are formed between the plurality of domains, and therefore, constant and slight electrolysis occurs at the plurality of the domains. Accordingly, the constant chemical reactions for generating the free chlorines occur at the plurality of domains on a small scale over the whole surface of each of the electrodes, and thus it is much easier to precisely control the concentration of the free chlorine at precisely lowered level.

That is, in case that electrolysis occurs at the electrodes which has a plurality of small multi-points (i.e., domains) on their surfaces facing each other and thus form a plurality of current paths between the multi-points, compared with the case that the electrolysis occurs at the electrodes only having simple flat surfaces facing each other, it was found that the more and smaller bubbles are generated with uniformly distributed during the electrolysis.

Especially, in the case that the multi-points of domains are formed on the electrodes, as electric charges are concentrated and flow along the paths between the multi-points of domains, the electric current can flow between the electrodes with the lowerly supplied voltage of 2.2V. or with the lower electric current, and the consumption of the electric power can be lowered, and thus the life of battery can be prolonged for a longer time. Most of all, instead of supplying lots of electric charges at the multi-point of domains at a time, electric charges are desired to be constantly and continuously supplied to the multi-point of domains to induce the electrolysis, so that the chemical reactions are constantly and uniformly realized because the reactants for generating HOCl can be reacted without any hindrances. Accordingly, when electrolysis occurs with the electrodes having the multi-points of domains facing each other in the same condition, the free chlorines are more constantly and slowly generated and thus it becomes easier to control the generation rate of the free chlorines thereby enabling to control and generate the free chlorines within targeted lower concentration thereof.

Similarly, during the supply of the DC voltage to the electrodes, by including the step of converting the direction of the electric current between the electrodes, the concentration of the free chlorines can be more precisely controlled to be lowered less than 6 ppm.

Herein, the electrode set comprises a plate-shaped positive electrode having a plurality of positive rods divided by a plurality of positive slots in one direction which are parallel with one another; and a plate-shaped negative electrode having a plurality of negative rods divided by a plurality of negative slots in one direction which are parallel with one another wherein a plurality of domains are formed by the areas overlapped in the perpendicular direction to the surface of the electrodes in condition that the positive electrode and the negative electrode are disposed in parallel, and that the positive rods are not disposed to be parallel with the negative rods.

From this construction, small electric current flows between the plurality of domains which are formed by the areas overlapped in the perpendicular direction to the surface of the positive electrode and the negative electrode, and the electrolysis constantly occurs at the uniformly distributed areas over the whole surface of the electrodes thereby enabling to precisely control the concentration of the free chlorines to the low level.

Herein, it is desirable that the positive rod and the negative rod are arrayed at right angle each other so that the distances among the domains and the sizes of the domains can be constant. The width of the positive rods is smaller than that of the positive slots while the width of the negative rods is smaller than that of the negative slots. Therefore, the domains of the negative electrode are arrayed more apart from the other domains of the negative electrode than the size of the domains. Further, the reactants required to generate the free chlorines are more distributed and thus the reactants react uniformly over the surface of the electrodes.

On the other hand, the electrodes include a plurality of positive projections protruded from the positive electrode; and a plurality of negative projections facing the each of the positive projections and protruded from the negative electrode, wherein the plurality of domains are formed on the top surface of the projections facing each other. The projections can be formed of cone shape or circular column shape or other form. In case that the domains are formed of the projections, the same or similar effects to the described above can be obtained.

Herein, the conversion period for changing the direction of current between the electrodes is desirable to be set between 1 second and 20 seconds. Also, when the amount of the normal saline is 10 ml to 100 ml, the normal saline can be manufactured with a portable apparatus by a customer level. At this case, the medical normal saline with 0.17 ppm to 6 ppm concentration of the free chlorines can be obtained by supplying DC current for 10 seconds to 60 seconds.

Advantageous Effects

As described above, the present invention provides a method for manufacturing sterilized normal saline for medical purpose with effective sterilizing efficacy comprising: a step of disposing at least one electrode set immersed in saline solution of pH 4.0 to pH 7.5 including a pair of positive electrode and negative electrode with flat surface separated from each other by an interval between 1 mm and 3 mm, the flat surfaces of the electrodes facing each other; a step of supplying 30 mA to 200 mA direct current to the electrodes by applying 2.4V to 3.3V DC power to the electrodes; wherein free chlorine is generated as having concentration range between 0.17 ppm and 6 ppm from electrolysis between electrodes, whereby the medical normal saline with lower concentration of the free chlorines can be stably and reliably obtained.

Further, the present invention enables to apply the medical normal saline to sensitive patients because the medical normal saline is manufactured by strictly and precisely controlling the concentration of the free chlorines within the lower range, and thus does not have any stimulus on the sensitive part of body such as mucosa of lung, eye, nose, skin and does not have offensive smell owing to much of chlorine.

Also, the present invention enables patients or customers to manufacture the medical normal saline by electrolysis for themselves at any time and at any place, which contains the precisely controlled concentration of the free chlorines, and thus, enables patients or customers to apply the fresh medical normal saline with more sterilizing efficacy for their purpose directly after manufacturing it, thereby maximizing the curing efficacy.

And, the present invention enables to use battery of a portable apparatus for manufacturing the medical normal saline for longer time because the electrolysis occurs by applying low voltage and low current to the electrodes thereby reducing the consumption of the electric power.

Also, the present invention uses subacid or neutral water of pH 4.0 to pH 7.5 during the electrolysis so as to maximize the content of HOCl having sterilizing efficacy of 80 times more than $OCl^-$, and provides a medical normal saline having high sterilizing efficacy.

BRIEF DESCRIPTION OF THE DRAWINGS

Accordingly, the present invention will be understood best through consideration of, and reference to, the following Figures, viewed in conjunction with the Detailed Description of the Preferred Embodiment referring thereto, in which like reference numbers throughout the various Figures designate like structure and in which:

FIG. 8 is a cross-sectional view by cut-line VI-VI.

FIG. 9 is a front view of other construction of electrodes applicable to the electrodes of FIG. 4.

BEST MODE FOR CARRYING OUT THE INVENTION

Figure 1:
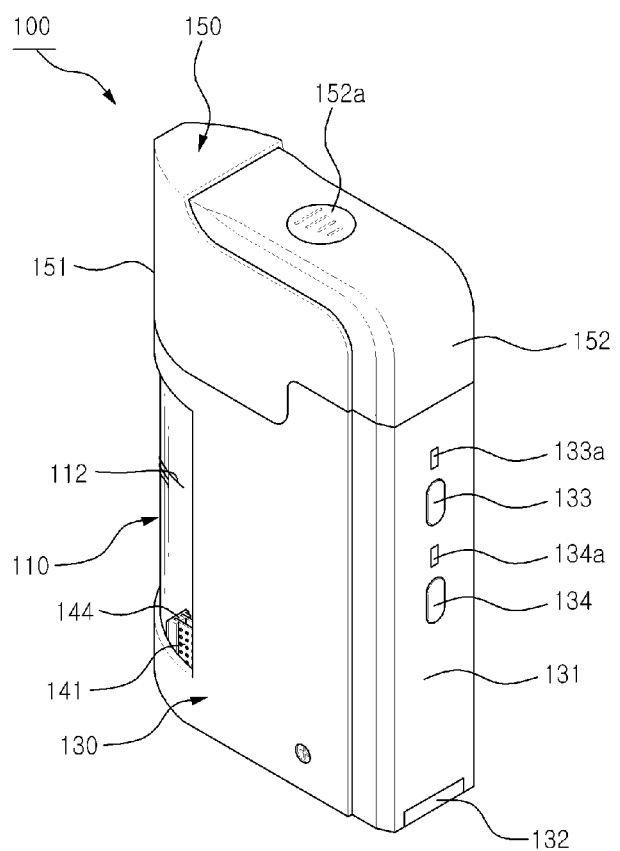
FIG. 1 is a perspective view of an apparatus for realizing the medical sterilizing normal saline in accordance with one embodiment of the present invention.
Figure 2:
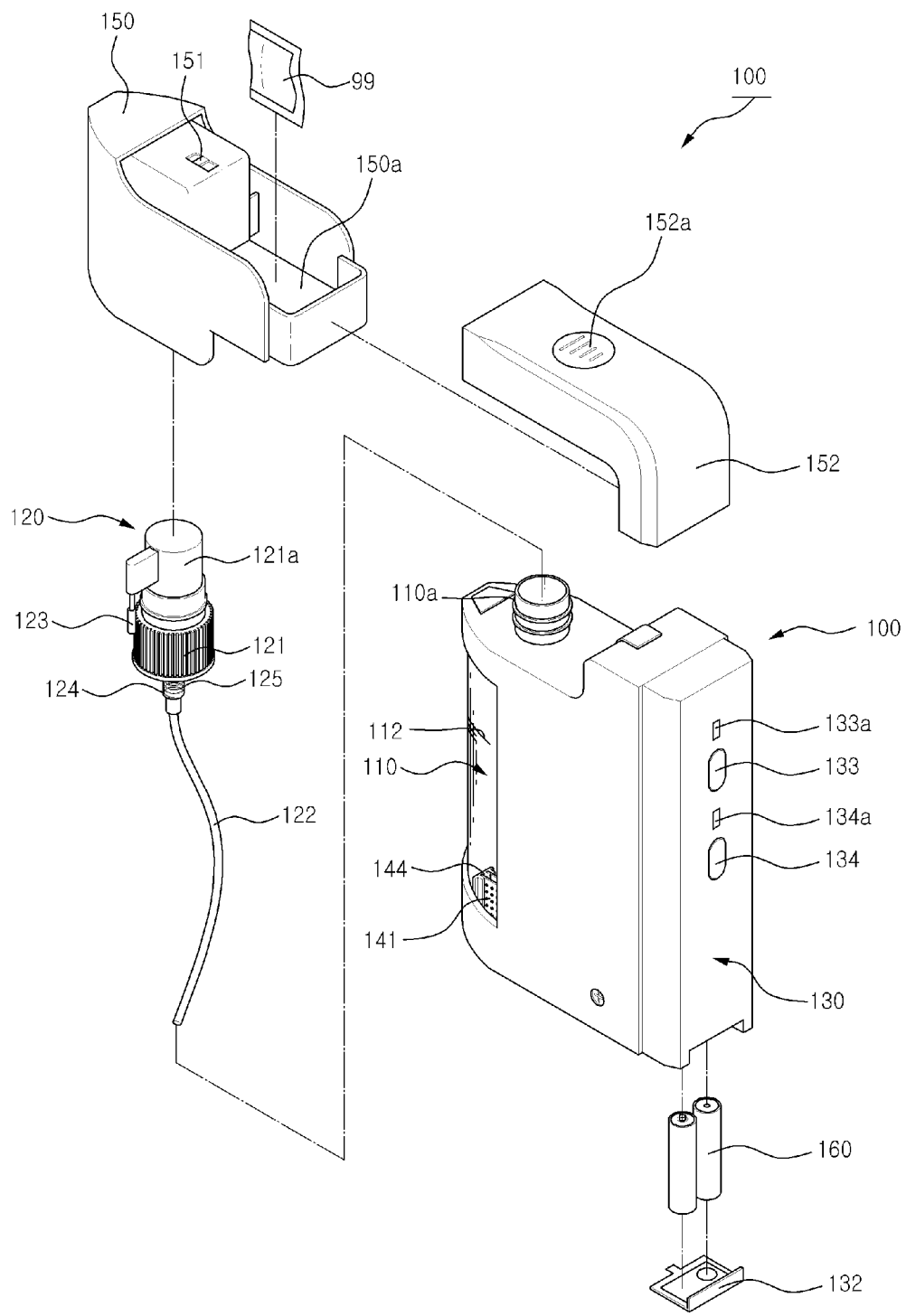
FIG. 2 is a exploded perspective view of FIG. 1
Figure 3:
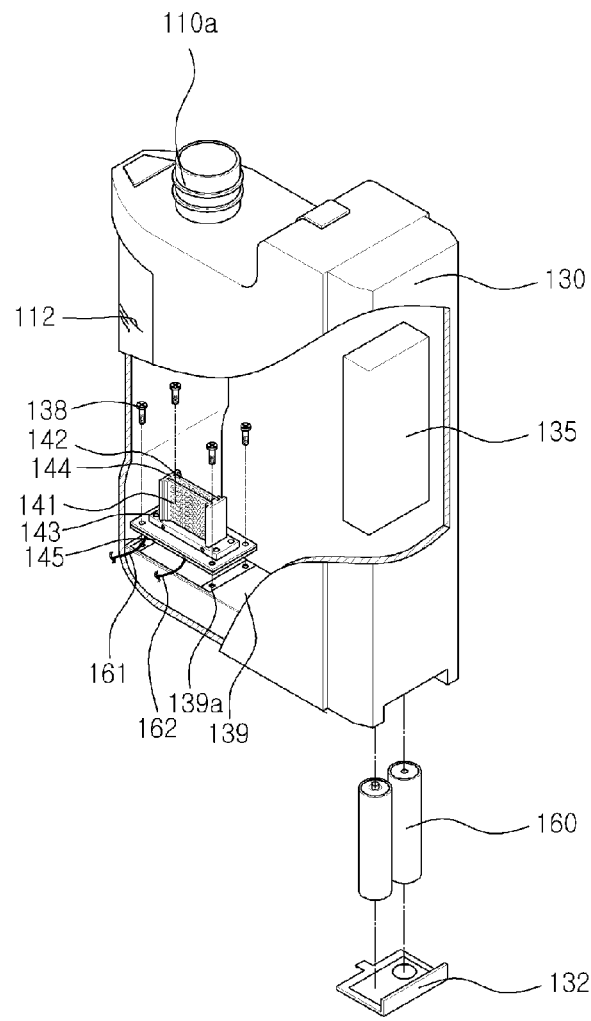
FIG. 3 is a partly sectional perspective view of FIG. 1
Figure 4:
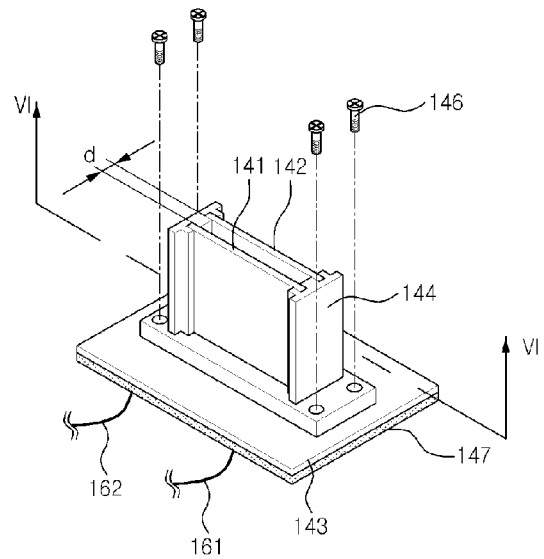
FIG. 4 is a perspective view of the electrodes of FIG. 1

The foregoing and other objects, features, aspects and advantages of the present invention will become more apparent from the following detailed description of the present invention when taken in conjunction with the accompanying drawings.

In describing the present invention, detailed description of laid-out function or structure is omitted in order to clarify the gist of the present invention.

As shown in the FIGS. 1 to 6, the apparatus for manufacturing sterilized normal saline in accordance with one embodiment of the present invention comprises: a container 110 for accommodating the water for manufacturing sterilized normal saline; a spraying unit 120 for spraying the sterilized normal saline to a wound area or inside of a nose; a body 130 holding the container 110 and a control circuit; an electrode set 140 immersed under the saline solution in the container 110 for generating oxidants including HOCl by electrolysis; a cover 150 for covering the upper part of the body 130; and a battery 160 of a power supply for supplying electric power to the electrode set 140.

The container 110 is formed for accommodating saline solution of about 0.9% salt concentration by mixing drinking water and salt. In order to make the about 0.9% salt concentrated saline solution, scale is indicated on the surface of the container 110 for accommodating the exact amount of water (e.g., 50 ml or 100 ml) of which pH is 4.0 to 7.5. As the pH of the accommodated solution is between pH 4.0 to 7.5, most of the free chlorines generated therein form HOCl with high sterilizing efficacy.

Also, in order to manufacture medical normal saline with 0.9% salt concentration, normal saline is poured to the container 110 via the entrance 110*a* until the amount of the normal saline in the container 110 reaches the indicated scale. Herein, instead of directly pouring the normal saline into the container 110, after pouring tap water of neutral or subacid into the container 110 firstly, the normal saline can be manufactured by mixing the water with salt which is released from a salt package containing the suitable amount for making water be normal saline.

The spraying unit 120 includes a plug 121 combined with the entrance 110*a* of the container 110 for isolating the accommodated solution from the outside and having a button reciprocally movable, a chamber 124 having a changeable volume in accordance with the reciprocal movement of the button so as to suck up the sterilized solution from the container 110, a spring 125 plated with platinum on its surface and installed compressed in the chamber 124 so that the button can return to its original position, a spraying pipe which is a passage of the sterilizing water in the vertical direction for spraying the sterilized normal saline from inside of the container 110 to the outside, a spray 123 for spraying the sterilized normal saline formed on the outer surface of the plug 121.

Herein, in order to spray the sterilized normal saline to outside through the spraying unit 120, a user presses the button of the apparatus downwardly, then the sterilized normal saline is pumped up to the spraying unit 120 through the spraying pipe 122 by a instantaneous volume change of the vacuum chamber 124, and the sterilized normal saline can be sprayed through the spraying unit 120 in a form of minute water drops. The normal saline in the container 110 may be supplied to a part of patients or customers in other ways.

The body 130 includes a body case 131 surrounding the container 110 so as to form the exterior of the apparatus 100, a battery cover 132 for opening or closing the battery accommodating part (not shown) for accommodating two 1.5V batteries for supplying DC current, a switch 133 for ordering to supply DC current to the electrode set 140 until the free chlorines are generated to the concentration of 0.17 ppm to 6 ppm, a first indicator 133a for indicating the state of operation by colors such as red, yellow or green, a circuit accommodation area 135 for installing a control circuit such as for supplying DC current to the electrode set 140, and a bottom area 139 forming the bottom surface of the container 110.

When user presses the operation switch 133, DC voltage is supplied to the electrode unit 140 for a preset time so that the preset amount of the free chlorines is generated. Specifically, when the operation switch 133 is pressed, DC current is supplied to the electrode set 140 about for 20 seconds so that the free chlorines are generated to be 3 ppm to 4 ppm concentration of the normal saline at 20° C. In this regard, in case that the operation switch 133 is pressed twice continuously, as the free chlorines may be generated more than the intended amount, when any signal is input by pressing the operation switch 133 more than 2 times within 2 minutes, a message relating thereto is indicated via the indicators 134, 134a by color signal or by sound signal.

As shown in FIGS. 4 to 8, the electrode set 140 includes a negative electrode plate 141, and a positive electrode plate 142 apart from the negative electrode plate by 2 mm, a support 143 to fix the pair of electrodes 141, 142, side support 144 to guide the pair of the electrodes 141, 142 when the electrodes are being fixed to the support 143 and to maintain the interval between the electrodes 141, 142, a bottom plate 145 of fixing the support 143, fixing bolts to fix the support 143 to the bottom plate 145, and a rubber packing plate 147 beneath the bottom plate 145 for preventing solution from permeating into the electric components.

Figure 5:
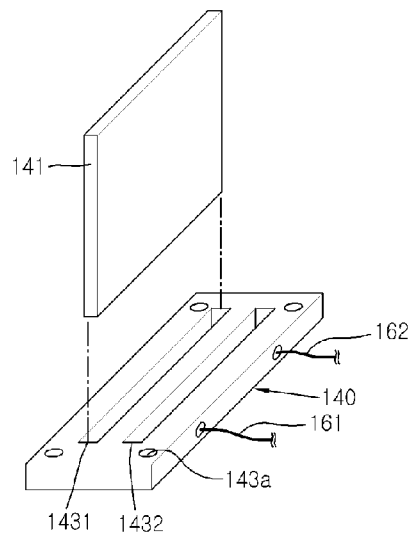
FIG. 5 is a dissembled perspective view of FIG. 4.

As shown in FIG. 5, the support 143 includes concave connection slot 1431 for fixing the negative electrode plate 141 and concave connection slot 1432 for fixing the positive electrode plate 142. As shown in FIG. 5, a negative electrode line 161 is connected to the connection slot 1431 of the negative electrode plate 141, and the positive electrode line 162 is connected to the connection slot of the positive electrode plate 142 inside of the support 143 so that simply inserting the electrode plates 141, 142 into the slots 1431, 1432 of the support 143 can provide an environment of supplying electric power to the electrode plates 131, 132. Therefore, when a platinum of the electrodes 141, 142 is used up, new electrodes can be replaceable by pulling the old electrodes 141, 142 from the support 143 and by inserting new electrodes 141, 142 into the slots 1431, 1432 of the support 143. Thus, the apparatus 100 can be usable semi-permanently.

Figure 6:
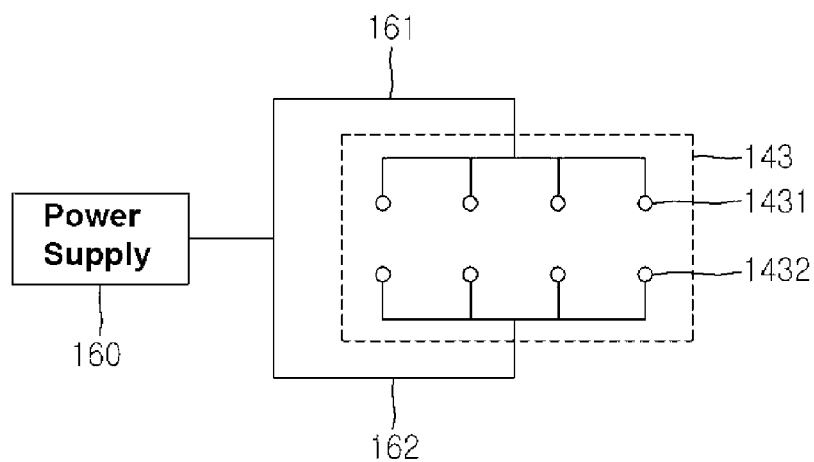
FIG. 6 is a circuit view showing power supply to the electrodes of the apparatus of FIG. 4.
Figure 7:
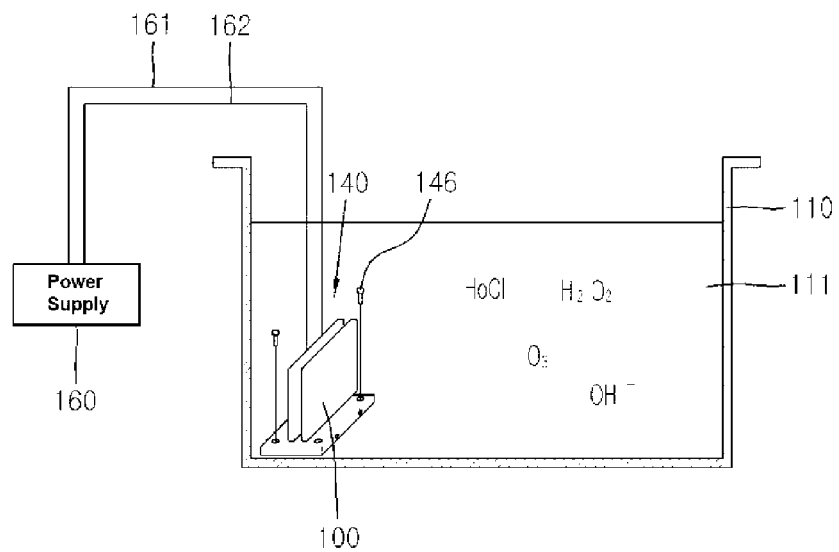
FIG. 7 is a flowchart for showing the operation principle of the apparatus of FIG. 1.

Also, the rubber packing plate 147 is attached beneath the bottom plate 145 and is placed between the bottom plate 149 and the bottom area 139 thereby preventing the normal saline from being leaked to the outside of the container 110. Herein, the rubber packing plate 147 may be formed of ring shape instead of plate shape, and thus attached to the circumstance of the bottom plate 139. The power supply lines 161, 162 are as shown in FIG. 6 connected with the inside of the body case 131 via the bottom plate 145, and thus transport DC current from the batteries 160.

Figure 10:
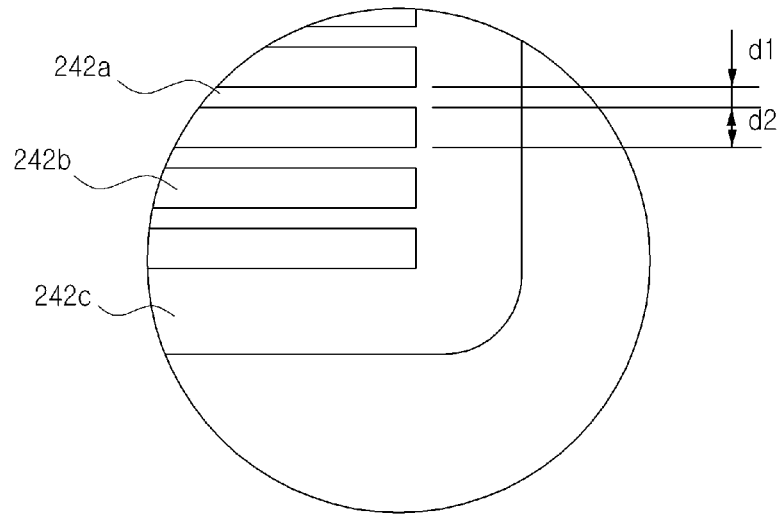
FIG. 10 is an enlarged part view of the second drawing of FIG. 9.
Figure 11:
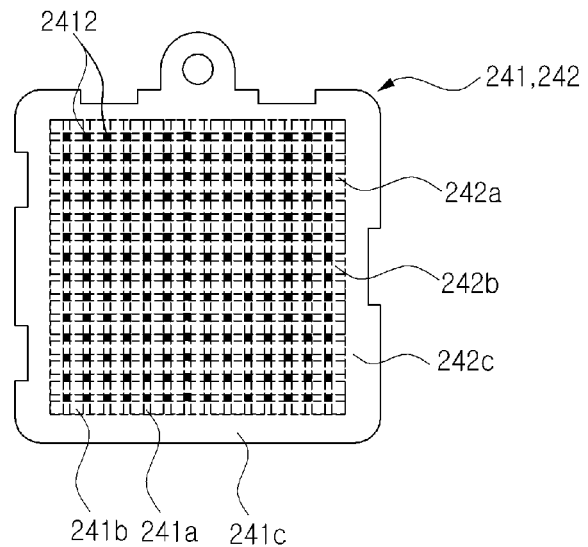
FIG. 11 is a schematic projected view when the first drawing of FIG. 9 is overlapped on the second drawing of FIG. 9.

Meanwhile, as shown in FIG. 9 to 11, the electrode set may be formed of a negative electrode 241 having a plurality of negative rods 241a divided by vertical slots 241b, and a positive electrode 242 having a plurality of positive rods 242a divided by horizontal slots 242b. Herein, as illustrated in FIG. 11, the negative rods 241a are arrayed with the positive rods 242a at right angle, and the plurality of domains facing each other are formed in the overlapped areas 2412 of the electrodes 241, 242 so that the plurality of electric current paths are formed between the domains of negative electrode 241 and the domains of positive domains 242. Therefore, although small amount of voltage is supplied to the plurality of domains which are distributed uniformly, the electric current flows therebetween, thereby extending the life of batteries 160. Further, as the electrolysis occurs by supplying small voltage to the domains of the electrodes 241, 242, the chemical reactions by reactants to generate HOCl occurs uniformly distributed. Therefore, as the amount of free chlorines such as HOCl is generated constantly and uniformly distributed compared with the case using flat shaped electrodes, the concentration of the free chlorines can be precisely controlled.

Herein, in order to prevent that the electrolysis occurs more vigorously along the circumstance area 241c, 242c of the electrode 241, 242 than at the plurality of domains 2412, coating layer is formed on the circumference area 241c, 242c except the area surrounded by x, y of FIG. 9. Also, the width d1 of the negative rod 241a and the positive rod 242a is smaller than the width d2 of the negative slot 241b and the positive slot 242b. Thus, the size of the domains 2412 becomes shorter than the distances between the domains 2412 whereby the reactants to generate HOCl can be uniformly and effectively distributed around current paths between the domains 2412 so that HOCl can be constantly generated by the adequate and continuous supply of the reactants. Therefore, the precise control of the HOCl is more easily achievable.

Figure 12:
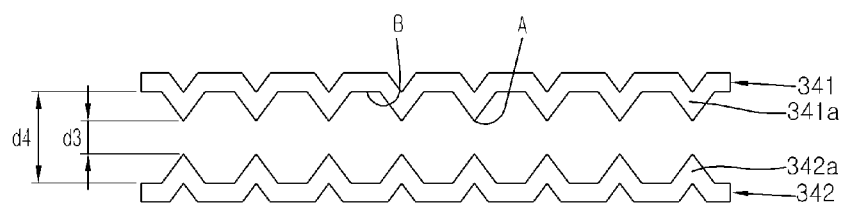
FIG. 12 is a view of another construction of electrodes applicable to the electrodes of FIG. 4.
Figure 13:
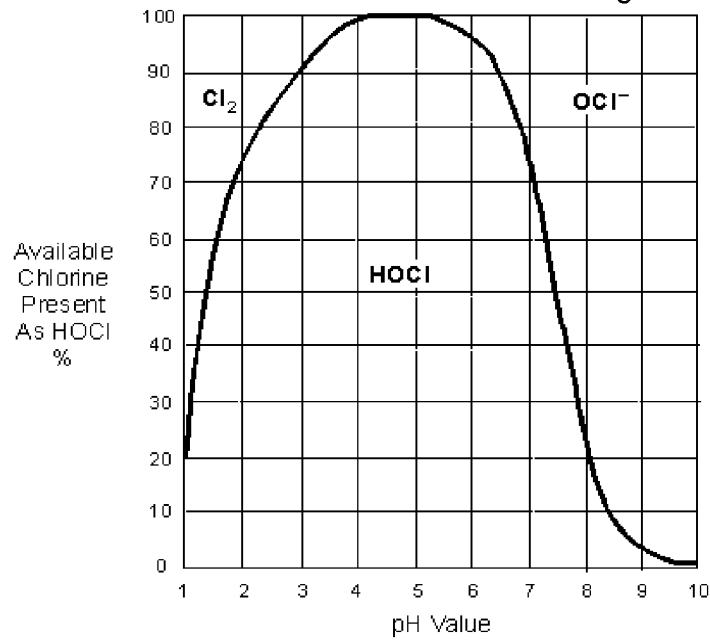
FIG. 13 is a graph of the relation between the form of free chlorine and pH at 20° C. and 100 m/l
Figure 14:
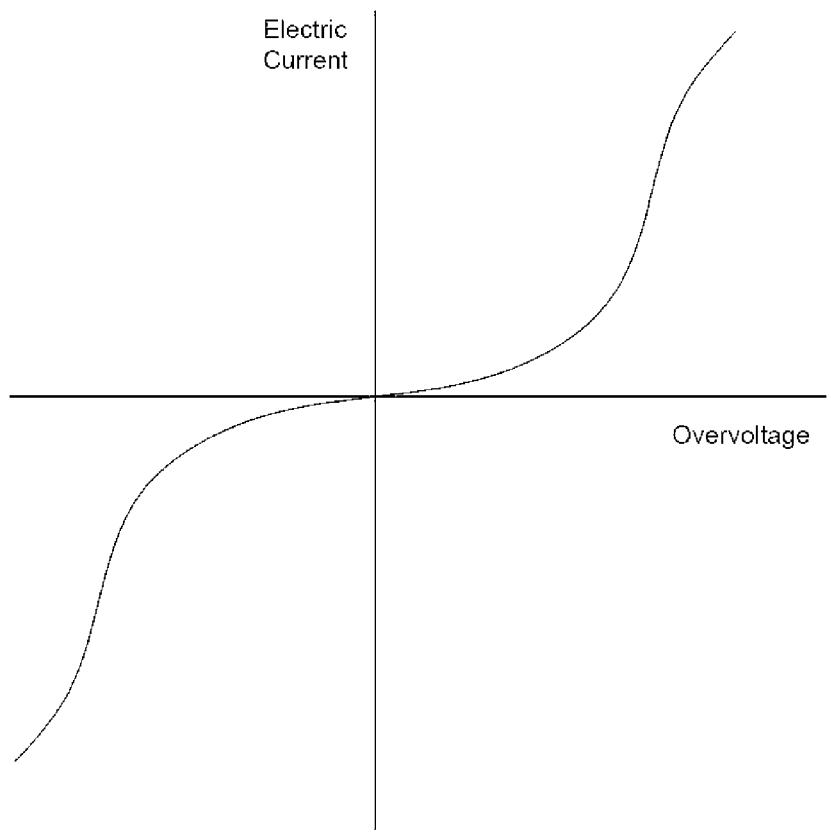
FIG. 14 is a graph of the relation of Butler-Volmer equation between overvoltage of electrodes and the current.

On the other hand, the electrode set having the plurality of domains facing each other may be formed as shown in FIG. 12. That is, the electrode set of FIG. 12 includes a negative electrode plate 341 having a plurality of negative projections 341a protruded thereon, a positive electrode plate 342 having a plurality of positive projections 342a the protruded thereon each of which faces each of the negative projections 341a, wherein the top areas A of both the plurality of negative projections 341a and the plurality of positive projections 342a form the plurality of domains facing each other. Similarly, the negative electrode plate 341 and the positive electrode plate 342 are fixed to the support 143 with maintaining a constant interval d4, and thus the negative projections 341a and the positive projections 342a on the facing surfaces B are separated each other by the interval d3, whereby electric charges are concentrated on the top areas A of the projections 341a, 342a. Therefore, although small voltage is supplied to the electrode 341, 342, the electric current can flow between the domains A facing each other of the electrodes 341, 342.

A platinum is plated on the surface of the electrodes 141, 142, 241, 242, 341, 342 thereby inducing the acute electrolysis.

The control circuit installed in the circuit accommodation area 135 controls to supply DC current to the electrodes 141, 142, 241, 242, 341, 342 for a preset time in accordance with the input of switch 133, and controls the indicators 133a, 134, 134a to indicate the operation state, and controls to convert the direction of the DC current in every 3 seconds to 7 seconds which is supplied to the electrodes 141, 142, 241, 242, 341, 342 thereby helping to precisely control the concentration of the free chlorines. Also, the control circuit includes a part for constantly supplying DC current to the electrodes 141, 142, 241, 242, 341, 342. Therefore, although a voltage of the new batteries 160 is initially 3.3V, only 2.2V to 2.5V is applied to the electrodes 141, 142, 241, 242, 341, 342 by the control circuit thereby making DC current between the electrodes 141, 142, 241, 242, 341, 342 as lower as possible. Herein, as the flat electrodes 141, 142 require higher voltage so as to make DC current flow therebetween, 2.4V is supplied to the electrodes 141, 142. On the other hand, as the electrodes 241, 242, 341, 342 require lower voltage so as to make DC current flow therebetween, 2.2V is supplied to the electrodes 241, 242, 341, 342.

Figure 15:
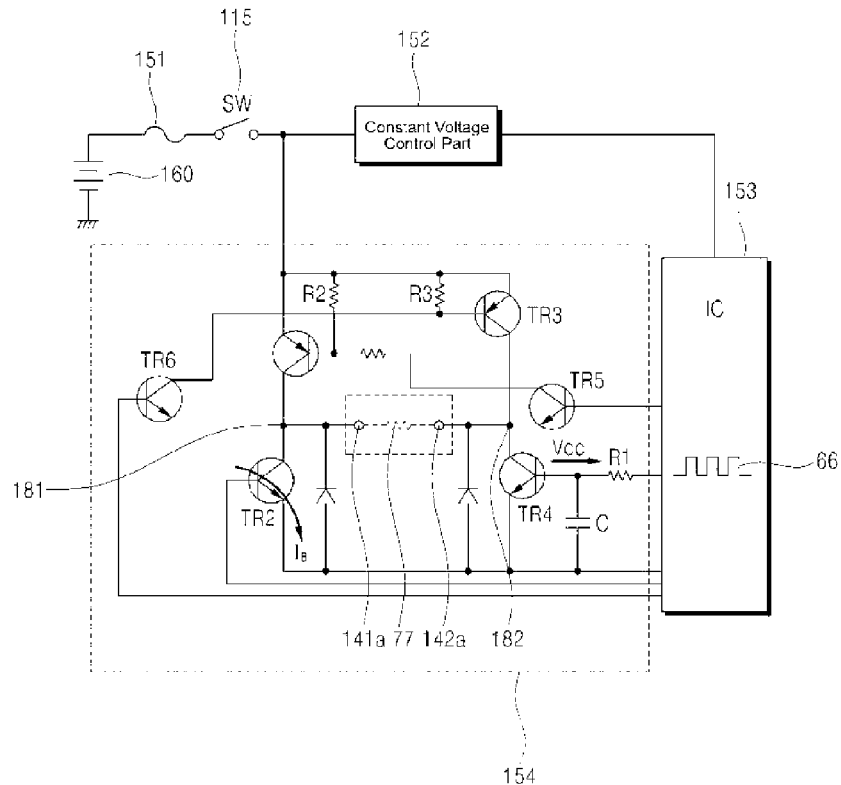
FIG. 15 is a view of a circuit for maintaining the current constantly between the electrodes in spite of the change of the salt concentration or the change of the voltage applied to the electrodes.
Figure 16:
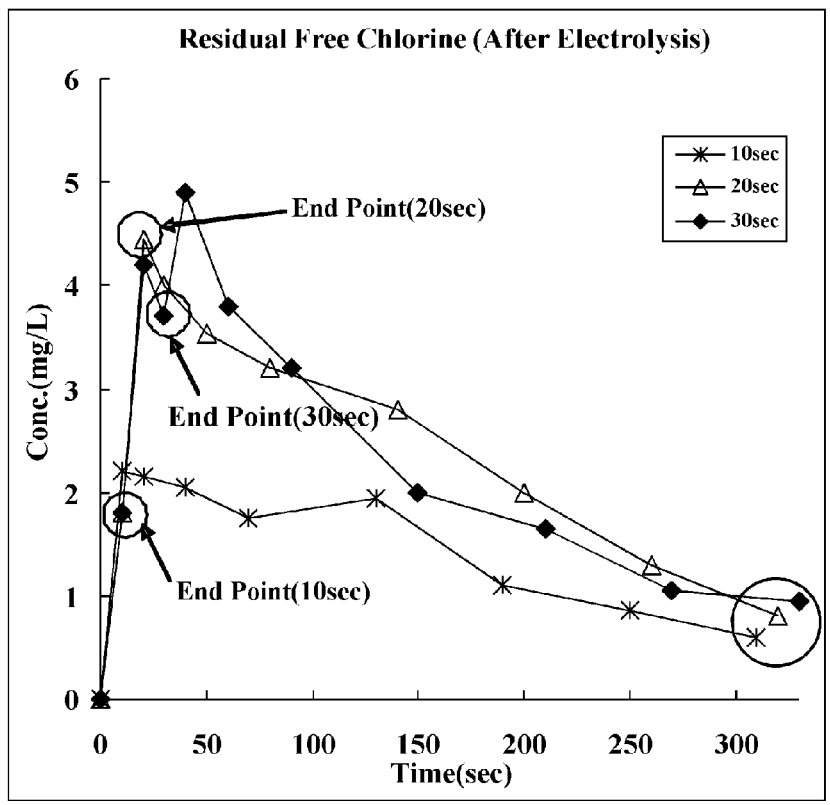
FIG. 16 is a graph of the amount of the free chlorine in accordance with the 20 seconds operation time.

Concretely, the circuit shown in FIG. 15 is to constantly maintain the DC current between the electrodes 141, 142, 241, 242, 341, 342 in spite of the consumption of batteries 160 and of the differences of the salt concentration. Also, the control circuit periodically converts the direction of DC current between the electrodes 141, 142, 241, 242, 341, 342, each of the initial negative electrodes 141, 241, 341 plays a role in the positive electrode, and similarly, each of the initial positive electrodes 142, 242, 342 also plays a role in the negative electrode, thereby preventing products of the chemical reaction from sticking onto the each of the electrodes 141, 142, 241, 242, 341, 342. In order to realize this operation, two pairs of transistors TR1, TR2, TR3, TR4 as a switch element are connected in parallel with each other, and the electrodes 141, 142, 241, 242, 341, 342 are placed between points 181, 182 which are located between the each pair of the transistors. Thus, when TR1 and TR4 are ON and when TR2 and TR3 are OFF, the DC current flows from the first point 181 to the second point 182, while TR1 and TR4 are OFF and when TR2 and TR3 are ON, the DC current flows from the second point 182 to the first point 181.

Herein, the saline solution between the electrodes 141, 142, 241, 242, 341, 342 plays a role in the resistance 111a of the circuit shown in FIG. 15. Thus, although a scale is indicated on the container 110 for accommodating the constant amount of saline solution, the salt concentration of the saline solution may be different by the carelessness of a user. Accordingly, the resistance 111a may be different, and the DC current also may be different from the preset value. In order to compensate the difference of DC current, actual DC current is sensed by a resistance R1 which is serially connected from the batteries 160.

For example, when TR1 and TR4 are ON and when TR2 and TR3 are OFF and thus DC current flows from the first point 181 to the second point 182, the DC current on the resistance R1 is sensed as a pulse form 66. Herein, when the DC current is higher than the preset value, if the base current IB is minutely raised, as a electric power is more consumed at TR1 and TR4, the width of the pulse 66 becomes smaller thereby lowering the voltage over the saline solution, and therefore, the DC current between the electrodes 141, 142, 241, 242, 341, 342 becomes smaller so that the targeted preset value of DC current can be applied to the electrodes 141, 142, 241, 242, 341, 342. Similarly, when the DC current is lower than the preset value, if the base current IB is minutely lowered, as a electric power is less consumed at TR1 and TR4, the width of the pulse 66 becomes bigger thereby raising the voltage over the saline solution, and therefore, the DC current between the electrodes 141, 142, 241, 242, 341, 342 becomes bigger so that the targeted preset value of DC current can be applied to the electrodes 141, 142, 241, 242, 341, 342. That is, the difference of the DC current in accordance with the differences of salt concentration can be compensated constantly by that IC 173 controls the base current $I_B$ to the transistors TR1, TR2, TR3, TR4 and thus controls the pulse width of DC current flowing between electrodes.

Similar operation principle is also applied in compensating the differences of DC current in accordance with the voltage drop due to the use of the batteries 160. Although the initial voltage of the batteries 160 is 3.3V, the voltage drops to 2.3V in accordance with a use of the batteries 160. Therefore, when DC current is applied to the electrodes 141, 142, 241, 242, 341, 342 for an initial preset time, as the voltage drops, the normal saline may be excessively sterilized when 3.3V is initially supplied thereto while the normal saline may be less sterilized when 2.3V is later supplied thereto. In order to solve this problem, the DC current is measured at the resistance R1 in-real time (herein, the DC current at R1 is the same at the electrodes 141, 142, 241, 242, 341, 342 because the resistance R1 is serially connected with the electrodes 141, 142, 241, 242, 341, 342). Thereafter, when the DC current at R1 is higher than the preset value to be supplied to the electrodes 141, 142, 241, 242, 341, 342, the minutely increased base current IB is applied to the transistors of which state is ON so that the voltage drop is induced to occur at the transistors, whereby the DC current can be maintained constantly in spite of the voltage change from the batteries 160.

From these constructions, although the salt concentration and the battery voltage may be inconsistent, the DC current applied to the electrodes can be constantly maintained, whereby the sterilized normal saline with the constantly lowly concentrated free chlorine such as HOCl can be reliably and stably obtained.

The cover 150 plays a role in covering the upper part of the body 130 and in accommodating the salt package of which amount is to weighed to make normal saline of about 0.9% salt concentration in the container 110. Thus, a user conveniently carries the required salt within the accommodating part 150a together with the apparatus 100. A lid 152 opens or closes the accommodating part 150a by combining with the combining part 151.

The batteries 160 as a power supply is formed of a pair of 1.5V rated voltage batteries. The batteries 160 supply 30 mA to 200 mA DC current to the electrodes 141, 142, 241, 242, 341, 342 via the power supply lines 161, 162 by the control circuit for the preset time. Without a user's control, the control circuit controls to periodically convert the direction of DC current in every 3 seconds to 7 seconds.

When the DC voltage is applied to the electrodes from the batteries 160, in accordance with the above procedures (1) to (5), the apparatus 100 manufactures the sterilized normal saline with 0.17 ppm to 6 ppm of low concentration of the residual concentration, wherein most of the free chlorines are formed of HOCl.

Hereinafter, the principle of the apparatus for manufacturing sterilized normal saline in accordance with the present of the invention will be described.

When a user manufactures sterilized normal saline using the apparatus 100, the user inputs subacid or neutral tap water and the salt in the package into the container 110 and mix them to make about 0.9% saline solution. Thereafter, the power is supplied via the slots 1431, 1432 to the electrodes 341, 342. Herein, a current is measured at the resistance R1 which is serially connected with the batteries 160, and after comparing the measured current with the preset current, the DC current to the electrodes 341, 342 is compensated by controlling the base current IB to the transistors by the difference between the measured current and the preset current.

Herein, the electric charges supplied to the electrodes 341, 342 are concentrated on the projections 341a, 342a facing each other. Thus, the electrolysis occurs at the plurality of current paths between the projections 341a,342a facing each other whereby the reactants of the electrolysis can be effectively reacted. The oxidants in the normal saline such as ozone, $H_2O_2$, HOCl, OCl$^-$, OH radicals generated by the electrolysis sterilize and kill germs, protein, fungi, bacteria, etc. within a short time. Especially, as the normal saline is neutral or subacid, most of the low concentrated free chlorines are formed of HOCl which has strong sterilizing efficacy thereby enabling to apply to the medical purpose and achieving highly improved sterilizing effect.

The apparatus 100 necessarily requires the only electrode set 241, 242, 341, 342 with plural domains A, 2412 facing each other, and thus can be constructed as a small portable one enough for a user to carry conveniently.

Hereinafter, the example of the sterilized normal saline in accordance with a first embodiment of the present invention will be described.

$1^{st}$ Embodiment

The electrodes 141,142 are formed of a plate-shape having its surface area of 1225 mm$^2$ which are plated with platinum and arrayed apart by an interval d of 2 mm from each other and immersed in the normal saline of 100 ml having pH 6.45±0.2. Also, DC current is supplied to the electrodes 141, 142 for 20 seconds with periodically converting the direction of the DC current in every 5 seconds. The concentration of the free chlorines was measured for 5 times with respect to the voltage change as shown in the following Table-2.

TABLE 2

| No. | Voltage Supply ($V_{DC}$) | DC Current (mA) | Average Concentration of Free chlorines | Standard Deviation of Concentration of Free chlorines |
|---|---|---|---|---|
| 1-1 | 2.2 | Not flow | — | — |
| 1-2 | 2.4 | 80 | 1.20 | 0.45 |
| 1-3 | 2.7 | 160 | 2.10 | 0.71 |
| 1-4 | 3.3 | 200 | 3.04 | 0.81 |
| 1-5 | 3.5 | 350 | 5.81 | 1.24 |
| 1-6 | 4.5 | 520 | 7.14 | 1.72 |

As shown in the experimental result Table-2, DC current cannot flow between the electrodes 141, 142 when DC 2.2V is supplied to the electrodes 141, 142, while average DC current of 80 mA flows between the electrodes 141, 142 when DC 2.4V is supplied thereto thereby generating very low concentrated (i.e., average 1.2 ppm) free chlorines. Average DC 200 mA flows between the electrodes 141, 142 in accordance with the supply of DC 3.3V and thus generates the still low concentrated (i.e., average 3.04 ppm) free chlorines. However, when DC 3.5V is supplied to the electrodes 141, 142, average DC current of 350 mA which is suddenly raised flows between the electrodes 141, 142 thereby generating the 5.81 ppm concentrated free chlorines. That is, in case that DC 3.5V slightly higher than DC 3.3V is supplied to electrodes 141, 142, the DC current between the electrodes 141, 142 is sharply. Although this concentration of 5.81 ppm is slightly less than 6 ppm, in view that the standard deviation is relatively higher value of 1.24, it can be concluded that the supply of DC 3.5V cannot guarantee the free chlorines less than 6 ppm.

$2^{nd}$ Embodiment

The width d1 of rods 241a, 242a of the electrodes 241,242 are formed of 0.7 mm, and the width d2 of slots 241b, 242b of the electrodes 241,242 are formed of 1.3 mm. The electrodes 241,242 are arrayed so that the negative rods 241a are positioned at right angle with the positive rods 242a. Each of the center areas including the domains (i.e., whole surface area of the rods and slots) surrounded by the x, y of FIG. 9 is 841 mm$^2$ respectively and are plated by platinum, and the other surface areas (i.e., circumstance area 241b, 242b excluding the center area) of the electrodes 241, 242 are coated by insulating layer so as to prevent the electrolysis from occurring at the circumference areas 241b, 242b. The electrodes 241, 242 are arrayed apart by 2 mm from each other and immersed in the normal saline of 50 ml having pH 6.37±0.2. Also, DC current is supplied to the electrodes 241, 242 for 20 seconds with periodically converting the direction of the DC current in every 5 seconds. The concentration of the free chlorines was measured for 5 times with respect to the voltage change as shown in the following Table-3.

TABLE 3

| No. | Voltage Supply ($V_{DC}$) | DC Current (mA) | Average Concentration of Free chlorines (ppm) | Standard Deviation of Concentration of Free chlorines |
|---|---|---|---|---|
| 2-1 | 2.1 | Not flow | — | — |
| 2-2 | 2.2 | 40 | 1.01 | 0.21 |
| 2-3 | 2.4 | 50 | 1.62 | 0.31 |
| 2-4 | 2.6 | 65 | 2.83 | 0.25 |
| 2-5 | 2.7 | 75 | 3.04 | 0.33 |
| 2-6 | 2.9 | 85 | 3.20 | 0.30 |
| 2-7 | 3.0 | 100 | 3.57 | 0.66 |
| 2-8 | 3.2 | 120 | 4.30 | 0.78 |
| 2-9 | 3.4 | 160 | 5.57 | 1.51 |

As shown in the experimental result Table-3, DC current cannot flow between the electrodes 241, 242 when DC 2.1V is supplied to the electrodes 241, 242, while average DC current of 40 mA flows between the electrodes 241, 242 when DC 2.3V is supplied thereto thereby generating very low concentrated (i.e., average 1.01 ppm) free chlorines. Average DC 120 mA flows between the electrodes 241, 242 in accordance with the supply of DC 3.2V and thus generates the still low concentrated (i.e., average 4.3 ppm) free chlorines. However, when DC 3.3V is supplied to the electrodes 241, 242, average DC current of 160 mA which is suddenly raised flows between the electrodes 241, 242 thereby generating the 5.57 ppm concentrated free chlorines. That is, in case that DC 3.4V slightly higher than DC 3.2V is supplied to electrodes 241, 242, the DC current between the electrodes 241, 242 is sharply increased in accordance with Butler-Volmer Equation. Although this concentration of 5.57 ppm is slightly less than 6 ppm, as the standard deviation is relatively higher value of 1.51, it can be concluded that the supply of DC 3.5V cannot guarantee the free chlorines less than 6 ppm.

Although not shown in the above table-3, regarding the small amount of less than 150 ml normal saline, it is confirmed by the experiment that the amount of the free chlorines generated by the electrolysis increases in the same way to the above result except for longer operation time.

$3^{rd}$ Embodiment

The width d1 of rods 241a, 242a of the electrodes 241,242 are formed of 0.3 mm, and the width d2 of slots 241b, 242b of the electrodes 241,242 are formed of 0.8 mm. The electrodes 241,242 are arrayed so that the negative rods 241a are positioned at right angle with the positive rods 242a. Each of the center areas including the domains (i.e., whole surface area of the rods and slots) surrounded by the x, y of FIG. 9 is 841 mm$^2$ respectively and are plated by platinum, and the other surface areas (i.e., circumstance area 241b, 242b excluding the domain area) of the electrodes 241, 242 are coated by insulating layer so as to prevent the electrolysis from occurring at the circumference areas 241b, 242b. The electrodes 241, 242 are arrayed apart by 2 mm from each other and immersed in the normal saline of 50 ml having pH 6.45±0.2. Also, DC 2.7V is supplied to the electrodes 241, 242 for 20 seconds with changing the conversion period of the direction of the DC current. The concentration of the free chlorines was measured for 5 times with respect to the conversion period change as shown in the following Table-4.

TABLE 4

| No. | Current Direction Conversion Period (second) | DC Current (mA) | Average Concentration of Free chlorines | Standard Deviation of Concentration of Free chlorines |
|---|---|---|---|---|
| 3-1 | 1 | Cannot measure | 1.61 | 0.47 |
| 3-2 | 2 | Cannot measure | 2.16 | 0.51 |
| 3-3 | 5 | 70 | 2.97 | 0.40 |
| 3-4 | 7 | 70 | 3.40 | 0.89 |
| 3-5 | 12 | 70 | 3.73 | 0.51 |
| 3-6 | 15 | 70 | 4.11 | 0.61 |
| 3-7 | 18 | 70 | 4.63 | 0.66 |
| 3-8 | 19 | 70 | 4.80 | 0.78 |
| 3-9 | Not change | 70 | 5.53 | 0.95 |

The experimental result of Table-4 shows that the average concentration of the free chlorines becomes smaller as the conversion period becomes shorter. On the other hand, in case that the direction of the DC current is not changed for 20 seconds, it shows that the possibility of exceeding 6 ppm of the concentration thereof increases. However, in case that the conversion period becomes too short, the DC current cannot be measured but the deviation of the concentration thereof shows a little bit high. Therefore, it was concluded that 5 second period is the most suitable for maintaining the concentration below 6 ppm and for reducing the deviations of the concentration. That is, comparing the case of 5 second period with the case of not having the conversion period, the concentration of the free chlorines and the deviation thereof in the former case with the conversion period becomes a half than that in the later case without the conversion period.

Meanwhile, although the data is not shown in the above Table-4 for the simple flat electrodes 141, 142, it has been confirmed that a trend for the flat electrodes 141, 142 is similar with the above case. That is, the case of applying 5 second period to convert the direction of the DC current generates about the half amount of concentration of the free chlorines and shows the half deviations of the concentration distribution compared with the case of not applying the conversion period.

4$^{th}$ Embodiment

The experiments is to performed what effect is influenced by the changes of the width of the rods 241a, 242a and the width of the slots 241b, 242b on the concentration of the free chlorines. Similarly with the 2$^{nd}$ embodiment, the electrodes 241,242 are arrayed so that the negative rods 241a are positioned at right angle with the positive rods 242a. Each of the center areas including the domains (i.e., whole surface area of the rods and slots) surrounded by the x, y of FIG. 9 is 841 mm$^2$ respectively and are plated by platinum, and the other surface areas (i.e., circumstance area 241b, 242b excluding the center area) of the electrodes 241, 242 are coated by insulating layer so as to prevent the electrolysis from occurring at the circumference areas 241b, 242b. The electrodes 241, 242 are arrayed apart by 2 mm from each other and immersed in the normal saline of 50 ml having pH 6.45±0.2. Also, DC 3.0V is supplied to the electrodes 241, 242 for 20 seconds with changing the conversion period of the direction of the DC current. The concentration of the free chlorines was measured for 5 times with respect to the conversion period change as shown in the following Table-5.

TABLE 5

| No. | Width of Rod (mm) | Width of Slot (mm) | DC Current (mA) | Average Concentration of Free chlorines | Standard Deviation of Concentration of Free chlorines |
|---|---|---|---|---|---|
| 4-1 | 0.7 | 1.3 | 100 | 3.57 | 0.66 |
| 4-2 | 0.3 | 0.8 | 80 | 3.01 | 0.49 |
| 4-3 | 0.5 | 1.0 | 85 | 3.24 | 0.61 |
| 4-4 | 1.0 | 1.0 | 110 | 4.07 | 1.11 |

The experimental result of Table-5 shows that the DC current becomes smaller as the area of domains 2412 facing each other becomes smaller for a unit area and distributed widely for a unit area. Therefore, it can be concluded that it is more efficient for precisely controlling the concentration of the free chlorines to uniformly distribute the plurality of domains 2412 which are formed as small as possible.

The Sterilizing Effect of Normal Saline of the Present Invention

The sterilized normal saline of 35 ml having 0.85% salt concentration is manufactured by electrolysis for 20 seconds, and then has been applied only 30 seconds to germs of *Staphylococcus aureus* MRSA for Time Kill Test by Polymer Solutions Incorporated in U.S.A. The test result is as follows.

TABLE 6

| Initial CFU/ml | contents | 1$^{st}$ Test | 2$^{nd}$ Test |
|---|---|---|---|
| 2.8 × 10$^6$ | Living CFL | Less than 5 | Less than 5 |
| 2.8 × 10$^6$ | Killing percentage | 99.9998% | 99.9998% |
| 2.8 × 10$^6$ | Log$_{10}$ (reduction rate) | 5.75 | 5.75 |

Herein, CFL means the numbers of living germs, and CFU/mL means the number of living germs population. The above test result shows that the contact with the sterilized normal saline only for 30 seconds makes 99.9998% of the germs named of *Staphylococcus aureus* MRSA killed.

Also, the sterilized normal saline of 50 ml having 0.80% salt concentration is manufactured by electrolysis for 20 seconds and thus having 3 ppm to 4 ppm concentrated free chlorines has been applied to the following germs for Time Kill Test. The test result is as follows.

| Organism | Initial Count (CFU/mL) | IC Log$_{10}$ | Time Point | Rep. | Result (CFU/mL) | Log$_{10}$ Reduction | % Reduction |
|---|---|---|---|---|---|---|---|
| A *Aspergillus fumigatus* | 1.00E+07 | 7.00 | 30 sec. | 1 | 3.00E+04 | 2.52 | 99.700000% |
| | | | | 2 | 3.00E+04 | 2.52 | 99.700000% |

-continued

| Organism | Initial Count (CFU/mL) | IC Log$_{10}$ | Time Point | Rep. | Result (CFU/mL) | Log$_{10}$ Reduction | % Reduction |
|---|---|---|---|---|---|---|---|
| B | 9.10E+07 | 7.96 | 30 sec. | 1 | 3.00E+04 | 3.48 | 99.967033% |
| Rhizopus oryzae | | | | 2 | 3.00E+04 | 3.48 | 99.967033% |
| C | 7.80E+05 | 5.89 | 30 sec. | 1 | 5.60E+03 | 2.14 | 99.282051% |
| Haemophilus influenae | | | | 2 | 4.50E+03 | 2.24 | 99.423077% |
| D | 8.60E+05 | 5.93 | 30 sec. | 1 | 4.30E+03 | 2.30 | 99.500000% |
| Strptococcus pneumoniae | | | | 2 | 5.10E+03 | 2.23 | 99.406977% |
| E | 9.80E+05 | 5.99 | 30 sec. | 1 | 5.20E+03 | 2.28 | 99.469388% |
| Strptococcus pyogenes | | | | 2 | 5.70E+03 | 2.24 | 99.418367% |
| F | 1.60E+06 | 6.20 | 30 sec. | 1 | 7.20E+04 | 1.35 | 95.500000% |
| Candida albicans | | | | 2 | 6.30E+04 | 1.40 | 96.062500% |
| G | 7.40E+07 | 7.87 | 30 sec. | 1 | 4.00E+01 | 6.27 | 99.999946% |
| Klebsiella pneumoniae | | | | 2 | 1.00E+01 | 6.87 | 99.999986% |
| H | 5.00E+07 | 7.70 | 30 sec. | 1 | 3.00E+04 | 3.22 | 99.940000% |
| Staphylococcus aureus MRSA | | | | 2 | 3.00E+04 | 3.22 | 99.940000% |

The A, B, C items of the listed germs indicate the fungus-kind germs, and the C, D, E, F, H items thereof indicate the bacteria-kind germs. The above test result shows that contact of the germs for 30 seconds with the sterilized normal saline of the present invention realizes the 95.5% to 99.9% killing effect.

Industrial Applicability

The medical sterilized normal saline of the present invention can be supplied to cure an allergy, rhinitis by transforming protein that is cause of allergy and can be sprayed to a throat for sterilizing inside of mouth and throat directly after being manufactured. Also, the sterilized normal saline can cure athletes' foot, an inflammation and a wounded area by spraying right after being manufactured. Further, the sterilized normal solution may be used to sterilize scurfy germs of hair, and may be used to kill germs or microbes in the shoes. Moreover, the sterilized normal saline may be applied to womb or vagina for curing contamination of HPV (human papillomavirus), teeth and germs, and mouth for gargling.

Figure 17:
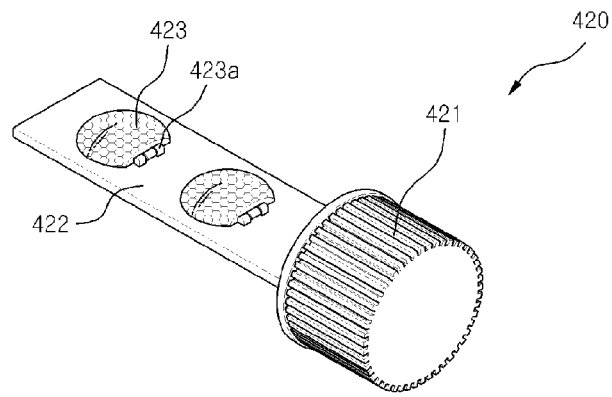
FIG. 17 and FIG. 18 are the perspective view of cleaning module of contact lenses combined with the inlet of the container of FIG. 2.
Figure 18:
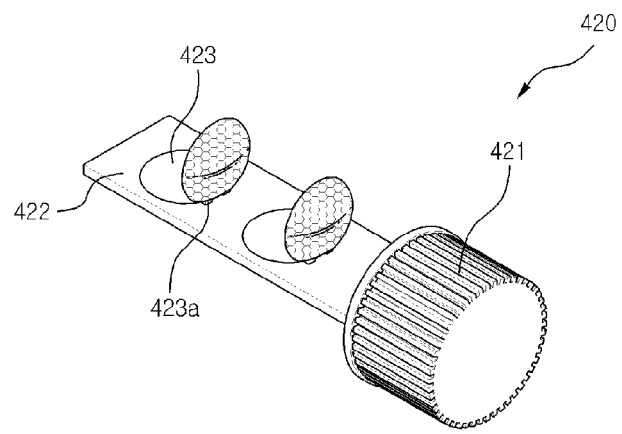

More concretely, the contact lens cleaning module 420 shown in FIGS. 17 and 18 may be used to fix to the entrance 110a of the container 110 for cleaning contact lens. That is, the contact lens module 420 includes a plug 421 for being fixed to the entrance 110a, an extending member 422 extended from the plug 421, a lens accommodating chamber 423 located at the extending member 422 so that lenses accommodated in the chamber 423 may be positioned in the sterilized normal saline. Herein, the wall of the lens accommodating chamber 423 is formed of wire so that the sterilized normal saline can enter the chamber 423 and sterilize the each of lenses in the chamber 423. Therefore, the oxidants including the free chlorines generated by the electrolysis sterilize or kill the germs, bacteria on the contact lenses while the hydrogen peroxide removes the protein on the surface of the contact lens.

Figure 19:
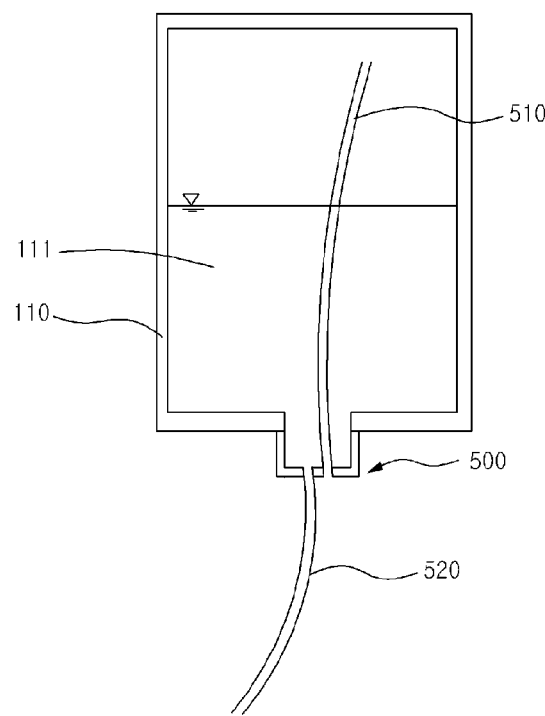
FIG. 19 is a schematic diagram of reversed state of the apparatus for manufacturing the medical normal saline with the plug.
Figure 20:
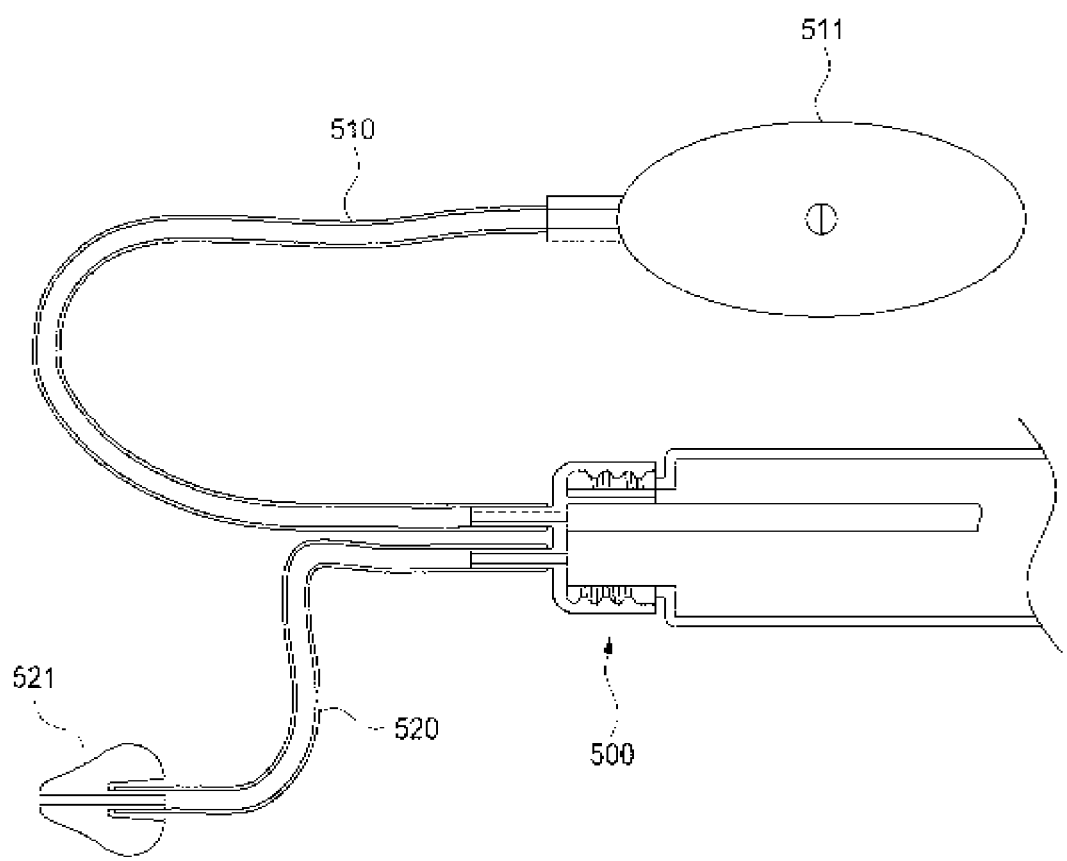
FIG. 20 is a detailed view of FIG. 19.

On the other hand, the supplying module 500 shown in FIGS. 19 and 20 can be used for supplying sterilized normal saline into deep place by fixing the inlet 110a of the container 110. Herein, the supplying module 500 comprises a plug to be fixed to the entrance 110a so as to intercept the air flow, an air tube 510 extended from the plug to over the surface of the normal saline when the container 110 is reversed, a fluid tube 520 extended from the lid to outside so as to make the sterilized normal saline flow out. When the supplying module is fixed to the inlet 110a and the apparatus 100 is reversed, although any driving means to exhaust or spray the normal saline does not included, in condition that the head of a user is located below feet, air is induced into the container 110 through the air tube 510, and thus, the sterilized normal saline is capable of coming from the container into the inside of nose or lung through the fluid tube 520. In order to prevent the fluid tube 520 from damaging the organs of human body, protect socket 521 having rounded shape is attached at the end of the fluid tube 520. Also, so as to prompt the exhausting of the sterilized normal saline from the container, air balloon is attached at the end of the air tube 510.

From this construction with a long tube 520, the medical sterilized normal saline can be supplied to a deep womb, a deep throat or a deep lung easily. Also, at the end of the tube 520, a mirror or lens may be attached so that a operator easily check whether the normal saline is being properly supplied.

Further, a holder shaped of a reversed cup may be attached at the end of the fluid tube 520 of the supplying module 500, and thus, it is possible to continuously supply the oxidants in the sterilized normal solution on skin for the time being such as 30 seconds to even 2 minutes. Herein, in order to make contact the newly generated oxidants with a user's skin, with constantly inducing electrolysis by continuously supplying low current to the electrode set 140, it is also possible to continuously supplying fresh oxidants into the holder from the container 110 by letting the sterilized normal saline leak via a small hole. Also, a sealing rubber packing is formed on the circumstances of the holder so as to prevent the sterilized normal saline from being leaked between the user's skin and inside of the holder.

On the other hand, when user wishes to supply the sterilized normal saline to the womb or vagina, it is desirable to use womb supplying module including a supply socket at the end of the supply tube wherein the supply socket has holes in the radial direction which allows sterilized normal saline to be evenly supplied into the womb. Although not shown in the figures, at least one spherical mirror is attached at the supply socket, and thus, the user can insert the supplying module for herself likewise the principle of endoscopy.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

The invention claimed is:

1. A method for manufacturing sterilized normal saline for medical purpose with sterilizing efficacy, the method comprising steps of:
disposing at least one electrode set in a saline solution of pH 4.0 to pH 7.5, the at least one electrode set including a pair of electrodes, each electrode having a facing surface with a plurality of domains, the plurality of domains on the facing surface of the one electrode oriented toward the plurality of domains on the facing surface of the other electrode, the plurality of domains on one electrode spaced between 1 mm and 3 mm from the plurality of domains on the other electrode; and
a step of supplying a direct current of 50 mA to 170 mA per 1000 mm$^2$ area of the facing surfaces of the electrodes by applying 2.2V to 3.2V DC power to the electrodes,
wherein the plurality of domains on each electrode has an area that is 4% to 25% of a total area of the facing surface of each electrode and a free chlorine is generated with a concentration range between 0.17 ppm to 6 ppm during electrolysis.

2. The method for manufacturing sterilized normal saline for medical purpose as claimed in claim 1, wherein the saline solution is normal saline.

3. The method for manufacturing sterilized normal saline for medical purpose as claimed in claim 2, the method further comprising a step of:
reversing the direction of the direct current flowing through the electrodes at least one time during electrolysis.

4. The method as claimed in claim 1, wherein the electrode set comprises:
a plate-shaped positive electrode having a plurality of positive rods divided by a plurality of positive slots in one direction which are parallel with one another; and
a plate-shaped negative electrode having a plurality of negative rods divided by a plurality of negative slots in one direction which are parallel with one another
wherein the plurality of domains are formed by the areas overlapped in the perpendicular direction to the surface of the electrodes when the positive electrode and the negative electrode are disposed in parallel so that the positive rods are not disposed to be parallel with the negative rods.

5. The method for manufacturing sterilized normal saline for medical purpose as claimed in claim 4, wherein the positive rods and the negative rods are disposed at right angles to each other.

6. The method for manufacturing sterilized normal saline as claimed in claim 4, wherein the width of the positive rods is narrower than the width of the positive slots, and the width of the negative rods is narrower than the width of the negative slots.

7. The method for manufacturing sterilized normal saline for medical purpose as claimed in claim 1, wherein the electrodes comprises,
a plurality of positive projections formed protrudedly on the positive electrodes; and
a plurality of negative projections formed protrudedly on the facing surface of the negative electrodes;
wherein the plurality of domains are formed by areas of the end surface of the positive projections and the negative projections facing each other.

8. The method for manufacturing sterilized normal saline for medical purpose as claimed in claim 1, wherein the direction of the direct current flowing through the electrodes is reversed every one second to every 20 seconds.

9. The method for manufacturing sterilized normal saline for medical purpose as claimed in claim 1, wherein the amount of the normal saline is 10 ml to 100 ml in and the normal saline solution is directly manufactured by a portable apparatus.

10. The method for manufacturing sterilized normal saline for medical purpose as claimed in claim 1, wherein the amount of the normal saline is 10 ml to 100 ml and the direct current is supplied to the electrodes for 10 to 60 seconds.

11. A method for manufacturing sterilized normal saline for medical purpose with sterilizing efficacy, the method comprising steps of:
disposing at least one electrode set in saline solution of pH 4.0 to pH 7.5, the at least one electrode set including a pair of electrodes, each electrode having a facing surface with a plurality of domains, the plurality of domains on the facing surface of the one electrode oriented towards the plurality of domains on the facing surface of the other electrode, the plurality of domains on one electrode spaced between 1 mm to 3 mm from the plurality of domains on the other electrode, wherein the plurality of domains of each electrode has an area that is 4% to 25% of a total area of the facing surface of each electrode; and
supplying direct current to the electrodes to perform electrolysis.

12. The method as claimed in claim 11, the method further comprising a step of:
reversing the direction of the direct current flowing through the electrodes at least one time during electrolysis.

* * * * *

UNITED STATES PATENT AND TRADEMARK OFFICE
CERTIFICATE OF CORRECTION

PATENT NO. : 8,518,233 B2
APPLICATION NO. : 12/449596
DATED : August 27, 2013
INVENTOR(S) : Kim It is certified that error appears in the above-identified patent and that said Letters Patent is hereby corrected as shown below:

On title page, insert item (30) Foreign Application Priority Data,

--February 26, 2007   (KR) 10-2007-0018791
  August 21, 2007   (KR) 10-2007-0084223--

Signed and Sealed this
Twenty-ninth Day of October, 2013

Teresa Stanek Rea
*Deputy Director of the United States Patent and Trademark Office*